United States Patent
Gay et al.

(10) Patent No.: US 9,434,944 B2
(45) Date of Patent: Sep. 6, 2016

(54) MODULATORS OF MIR-323-3P FOR THE PREVENTION OR TREATMENT OF RHEUMATOID ARTHRITIS

(75) Inventors: Steffen Gay, Zurich (CH); Mary Connolly, Offaly (IE); Caroline Ospelt, Zurich (CH)

(73) Assignee: UNIVERSITY OF ZURICH, Zurich (CH)

( * ) Notice: Subject to any disclaimer, the term of this patent is extended or adjusted under 35 U.S.C. 154(b) by 0 days.

(21) Appl. No.: 14/241,456

(22) PCT Filed: Aug. 31, 2012

(86) PCT No.: PCT/EP2012/067011
§ 371 (c)(1),
(2), (4) Date: Feb. 27, 2014

(87) PCT Pub. No.: WO2013/030362
PCT Pub. Date: Mar. 7, 2013

(65) Prior Publication Data
US 2014/0193366 A1    Jul. 10, 2014

(30) Foreign Application Priority Data
Aug. 31, 2011 (EP) ..................................... 11179646

(51) Int. Cl.
*C12N 15/11* (2006.01)
*C12N 15/113* (2010.01)
*C07H 21/04* (2006.01)

(52) U.S. Cl.
CPC ....... *C12N 15/113* (2013.01); *C12N 2310/113* (2013.01); *C12N 2310/315* (2013.01); *C12N 2310/3181* (2013.01); *C12N 2310/321* (2013.01); *C12N 2310/3231* (2013.01); *C12N 2310/3515* (2013.01)

(58) Field of Classification Search
CPC .......... C12N 15/113; C12N 2310/141; C12N 2501/65; C12Q 2600/178; C12Q 2525/207; G01N 2800/102
See application file for complete search history.

(56) References Cited

U.S. PATENT DOCUMENTS

| 6,251,601 | B1 | 6/2001 | Bao | |
|---|---|---|---|---|
| 7,435,719 | B2 | 10/2008 | Silbiger | |
| 2008/0171715 | A1* | 7/2008 | Brown et al. | 514/44 |
| 2012/0071541 | A1* | 3/2012 | Kawano et al. | 514/44 A |

FOREIGN PATENT DOCUMENTS

| WO | WO 2005/013901 A2 | 2/2005 |
|---|---|---|
| WO | WO 2006/137941 A2 | 12/2006 |
| WO | WO 2007/112754 A2 | 10/2007 |

OTHER PUBLICATIONS

Krutzfeldt et al., Silencing of microRNAs in vivo with 'antagomirs', 2005, Nature, vol. 438, pp. 685-689.*
Dancevic et al., Current and emerging therapeutic strategies for preventing inflammation and aggrecanase-mediated cartilage destruction in arthritis, 2014, Arthritis Research & Therapy, 16:429, pp. 1-11.*
Xu et al., MicroRNA-323-3p: a new biomarker and potential therapeutic target for rheumatoid arthritis, 2014, Rheumatology International, vol. 34, pp. 721-722.*
Li Jingyi et al: "Altered microRNA expression profile with miR-146a upregulation in CD4+ T cells from patients with rheumatoid arthritis", Arthritis Research and Therapy, vol. 12, No. 3, May 11, 2010,p. R81.
T. Nakasa et al: "A mini-review: microRNA in arthritis", Physiological Genomics, vol. 43, No. 10, May 26, 2011, pp. 566-570.
Angela Ceribelli et al: "MicroRNAs in rheumatoid arthritis", FEBS Letters, vol. 585, No. 23, May 4, 2011, pp. 3667-3674.
Esmerina Tili et al: "MicroRNAs, the immune system and rheumatic disease", Nature Clinical Practice Rheumatology, vol. 4, No. 10, Aug. 26, 2008, pp. 534-541.
Pandis Ioannis et al: "Identification of mi croRNA-221/222 and mi croRNA-323-3p association with rheumatoid arthritis via predictions using the human tumour necrosis factor transgenic mouse model", Annals of the Rheumatic Diseases, vol. 71, No. 10, Oct. 2012, pp. 1716-1723.
Connolly Mary et al: "MiR-323, a Novel MicroRNA in Rheumatoid Arthritis, Promotes the Activated Phenotype of Synovial Fibroblasts", Arthritis & Rheumatism, vol. 63, No. 10, Suppl. S, 1672, Oct. 2011, p. S654.
Drynda et al.. "Gene transfer of tissue inhibitor of metalloproteinases-3 reverses the inhibitory effects of TNF-alpha on Fas-induced apoptosis in rheumatoid arthritis synovial fibroblasts", J. Immunol. 174:6524-6531, 2005.
van der Laan et al., "Cartilage degradation and invasion by rheumatoid synovial fibroblasts is inhibited by gene transfer of TIMP-1 and TIMP-3", Gene Therapy, 10:234-242, 2003.
Ambion Anti-miR miRNA inhibitors product insert, Jun. 2010 (2 pages), available on line at appliedbiosystems.com/cms/groups/mcb_support/documents/generaldocuments/cms_084838.pdf.

* cited by examiner

*Primary Examiner* — Dana Shin
(74) *Attorney, Agent, or Firm* — JMB Davis Ben-David

(57) ABSTRACT

A miR-323-3p inhibitor is provided for the prevention or therapy of rheumatoid arthritis, comprising a sequence capable of forming a hybrid to miR-323-3p as an oligonucleotide or a vector from which such oligonucleotide is transcribed, or as a miRNA decoy or sponge.

9 Claims, 8 Drawing Sheets

(A)

(B)

(A)

(B)

(A)

(B)

(A)

(B)

MODULATORS OF MIR-323-3P FOR THE PREVENTION OR TREATMENT OF RHEUMATOID ARTHRITIS

CROSS-REFERENCE TO RELATED APPLICATIONS

This is the U.S. National Stage of International Application No. PCT/EP2012/067011, filed Aug. 31, 2012, which was published in English under PCT Article 21(2), which in turn claims the benefit of European Patent Application No. 11179646.2, filed Aug. 31, 2011.

FIELD

This invention relates to nucleic acid modulators of miR-323-3p for use in a method for the prevention and treatment of rheumatoid arthritis.

BACKGROUND

Micro RNA (miRNA) are short endogenous ribonucleic acid molecules that participate in the regulation of gene expression. miR-323-3p is a 21 nucleotide long regulatory microRNA (SEQ ID 1: CAC AUU ACA CGG UCG ACC UCU) which is derived from the 3' end of the precursor stem loop pre-miR-323 (SEQ ID 2: UUGGUACUUG GAGA-GAGGUG GUCCGUGGCG CGUUCGCUUU AUUUAUGGCG CACAUUACACGGUCGACCUCUUUGCAGUAU CUAAUC).

Rheumatoid arthritis (RA) is a chronic inflammatory autoimmune disease ultimately leading to joint destruction and disability. The invasion of synovial cells into articular cartilage and bone contributes significantly to joint destruction in RA. Activated synovial fibro-blasts (SF) are involved in this process. They attach to the cartilage surface and release matrix-degrading enzymes, importantly among them matrix metalloproteinases. Overexpression of tissue inhibitors of metalloproteinases (TIMPs) has been shown to reduce invasiveness of RA synovial fibroblasts (RASF) and inhibit their proliferation (van der Laan et al. 2003, Gene Therapy 10, 234-242).

Currently available medication for RA is aimed at slowing the disease progression and alleviating symptoms, but no curative treatment is available. Hence, the objective of the present invention is to provide safe and efficacious means for the prevention and treatment of rheumatoid arthritis. This objective is attained by the subject-matter of the independent claims.

The central feature of the invention is the surprising finding that miR-323-3p is significantly increased in rheumatoid arthritis and thereby involved in the up-regulation of pro-inflammatory cytokines and matrix metalloproteinases in synovial fibroblasts from patients with rheumatoid arthritis (RASF). miR-323-3p also potentiates cell migration, proliferation and adhesion, other key processes in the pathogenesis of RA. Furthermore, TIMP-3, which inhibits invasion of RASF in the cartilage (van der Laan, ibid.), is a direct target of miR-323-3p. The miRDB database accessible at mirdb.org lists 371 predicted targets for miR-323-3p on 30 Aug. 2011; no member of the TIMP family of proteins is among them.

SUMMARY

In summary, miR-323-3p is involved in the development of the activated phenotype of RASF. Thus, inhibitors of miR-323-3p are potent candidates for pharmacological intervention in rheumatoid arthritis.

According to a first aspect of the invention, a miR-323-3p inhibitor is provided for the prevention or therapy of rheumatoid arthritis. Such inhibitor comprises a hybridizing sequence of nucleotides, capable of forming a hybrid to miR-323-3p (SEQ ID 1) or its precursor (SEQ ID 2).

"Capable of forming a hybrid" in the context of the present invention relates to sequences that under the conditions existing within the cytosol of a mammalian cell are able to bind selectively to their target sequence. Such hybridizing sequences may be contiguously reverse-complimentary to the target sequence, or may comprise gaps, mismatches or additional non-matching nucleotides. The minimal length for a sequence to be capable of forming a hybrid depends on its composition, with C or G nucleotides contributing more to the energy of binding than A or T/U nucleotides, and the backbone chemistry.

"Nucleotides" in the context of the present invention are nucleic acid or nucleic acid analogue building blocks, oligomers of which are capable of forming selective hybrids with RNA oligomers (specifically with miR-323-3p) on the basis of base pairing. The term nucleotides in this context includes the classic ribonucleotide building blocks adenosine, guanosine, uridine (and ribosylthymin), cytidine, the classic deoxyribonucleotides deoxyadenosine, deoxyguanosine, thymidine, deoxyuridine and deoxycytidine. It further includes analogues of nucleic acids such as phosphotioates, 2'O-methylphosphothioates, peptide nucleic acids (PNA; N-(2-aminoethyl)-glycine units linked by peptide linkage, with the nucleobase attached to the alpha-carbon of the glycine) or locked nucleic acids (LNA; 2'O, 4'C methylene bridged RNA building blocks). The hybridizing sequence may be composed of any of the above nucleotides, or mixtures thereof.

The miR-323-3p inhibitor of the invention is able to abrogate or neutralize the anti-TIMP-3 effect of miR-323-3p.

Such modulator according to the invention may be a nucleic acid directed against and hybridizing to miR-323-3p, preferentially with neutralizing properties. It may be a single-stranded or double-stranded ribonucleic acid oligomer or a precursor thereof, or a deoxyribonucleic acid or analogue thereof, comprising a sequence tract complementary to miR-323-3p.

In some embodiments, the hybridizing sequence of the inventive miR-323-3p inhibitor comprises 8, 9, 10, 11, 12, 13, 14, 15, 16, 17, 18, 19, 20, 21, 22, 23, 24, 25, 26, 27, 28, 29 or 30 nucleotides.

In some embodiments, the hybridizing sequence is at least 80% identical, more preferred 85%, 90%, 92%, 94%, 95%, 96%, 97%, 98% or 99% identical to the reverse complimentary sequence of SEQ ID 1 or SEQ ID 2.

Identity in the context of the present invention is a single quantitative parameter representing the result of a sequence comparison position by position. Methods of sequence comparison are known in the art; the BLAST algorithm available publicly is an example.

In some embodiments, the hybridizing sequence comprises deoxynucleotides, phosphothioate deoxynucleotides, LNA and/or PNA nucleotides or mixtures thereof.

According to some embodiments, the hybridizing sequence comprises ribonucleotides, phosphothioate and/or 2'-O-methyl-modified phosphothioate ribonucleotides.

According to some embodiments, the hybridizing sequence comprises deoxynucleotides, phosphothioate deoxynucleotides, phosphothioate ribonucleotides and/or 2'-O-methyl-modified phosphothioate ribonucleotides.

According to some embodiments, the miR-323-3p inhibitor comprises a cholesterol moiety or a peptide. According to one embodiment, the hybridizing sequence is covalently attached to a cholesterol moiety or a peptide. Alternatively, the peptide may be part of a nucleic acid-peptide complex held together without covalent attachment by electrostatic or hydrophobic interaction. In one embodiment, the miR-323-3p inhibitor is a peptide comprising a TAT translocation sequence or a functional equivalent thereof.

In one embodiment, the miR-323-3p inhibitor is a complementary sequence of miR-323-3p such as, for example, the Ambion Anti-miR miRNA Inhibitor AM12418.

In some embodiments, the above ribo- or deoxyribonucleotide moieties, optionally protected against degradation by phosphothioate linkage and/or 2'O-methyl ethers, and/or LNA or PNA moieties, may be combined with cholesterol or peptide targeting and packaging moieties.

According to an alternative embodiment, the inventive miR-323-3p inhibitor comprises a transcribed sequence comprising a decoy sequence tract at least 90% identical to sequence of SEQ ID 1 or SEQ ID 2 under control of a polymerase promoter sequence operable in a mammalian cell. Upon transcription, the transcript will comprise a sequence tract forming the reverse complementary sequence of miR-323-3p or its precursor, or a sequence at least 90% identical and capable of forming a hybrid to miR-323-3p or its precursor. Such decoy transcript will then act like a "sponge" for miR-323-3p. According to one embodiment, the inhibitor comprises at least 5 decoy sequence tracts.

According to some embodiments, the decoy sequence tract is at least 85%, 90%, 92%, 94%, 95%, 96%, 97%, 98% or 99% identical to SEQ ID 1 or SEQ ID 2.

The inhibitor according to this embodiment may be, by way of non-limiting example, a virus or a naked DNA vector such as a plasmid or linear DNA fragment or micro-chromosome.

According to a second aspect of the invention, a virus particle is provided, comprising
 a transcribed sequence comprising a decoy sequence tract at least 90% identical to sequence of SEQ ID 1 or SEQ ID 2 or
 a sequence being capable of forming a hybrid to SEQ ID 1 or SEQ ID 2,
under control of a polymerase promoter sequence operable in a mammalian cell, for use in a method for the prevention or therapy of rheumatoid arthritis.

Such virus particle is capable of intracellular production of an inhibitor as described in the embodiments above. Preferred vectors are adenovirus or adeno-associated virus. Lentivirus vectors are alternative preferred embodiments.

Also provided is a pharmaceutical composition for the prevention or therapy of rheumatoid arthritis, comprising a miR-323-3p inhibitor or a virus particle according to the above aspects of the invention. Optionally, a pharmaceutically acceptable recipient will be present. Preferred recipients are liposomes, peptides capable of condensing nucleic acids for intracellular uptake, or polymers such as polyethylene imine (PEI). Particularly preferred is a neutral nanoliposome, such as 1,2-dioleoyl-sn-glycero-3-phosphatidylcholine (DOPC). Alternatively, nanoparticles comprising an inventive miR-323-3p inhibitor may be formed by chitosan.

Similarly within the scope of the present invention is a method for treating rheumatoid arthritis in a patient in need thereof, comprising administering to the patient a miR-323-3p inhibitor or a virus particle according to the above description.

Similarly, a dosage form for the prevention or treatment of rheumatoid arthritis is provided, comprising an inhibitor according to one of the above aspects of the invention.

Dosage forms may be for enteral administration, such as nasal, buccal, rectal, transdermal or oral administration, or as an inhalation form or suppository. Alternatively, parenteral administration may be used, such as subcutaneous, intravenous, intrahepatic or intramuscular injection forms. Optionally, a pharmaceutically acceptable carrier and/or excipient may be present.

Said pharmaceutical compositions comprise from approximately 1% to approximately 95% active ingredient, preferably from approximately 20% to approximately 90% active ingredient.

An intravenous injection form of a said pharmaceutical composition is preferred. According to a particularly preferred embodiment, solutions of an inhibitor according to any of the above aspects of the invention can be made up shortly before use as an injection form. Similarly, suspensions or dispersions, especially isotonic aqueous solutions, dispersions or suspensions may be employed. Said pharmaceutical compositions may be sterilized and/or may comprise excipients, for example preservatives, stabilizers, wetting agents and/or emulsifiers, solubilizers, viscosity-increasing agents, salts for regulating osmotic pressure and/or buffers and are prepared in a manner known in the art, for example by means of conventional dissolving and lyophilizing processes.

A pharmaceutical composition comprising modulators according to one of the above aspects can be administered alone or in combination with one or more other therapeutic agents. A combination therapy may take the form of fixed combinations of said pharmaceutical composition and one or more other therapeutic agents known in the prevention or treatment of rheumatoid arthritis. Administration may be staggered; alternatively the drugs may be given independently of one another, or in the form of a fixed combination.

Preferred combination partners to form a combination therapy with the inhibitors of the invention are RA disease-modifying anti-rheumatic drugs (DMARDs) such as azathioprine, cyclosporine A, cyclophosphamide, D-penicillamine, hydroxochloroquine, leflunomide, methotrexate, minocycline or sulfasalazine.

More preferred combination partners are TNFa-blockers such aus etanercept, infliximab, adalimumab, certolizumab pegol or golimumab, IL-1 blockers such as anakinra, CD-20 blockers such as rituximab, CTLA-4/B7 interfering agents such as abatacept or IL-6 blockers such as tocilizumab.

Likewise, a method for the manufacture of a medicament for use in a method for the prevention or treatment of rheumatoid arthritis is provided, comprising the use of an inhibitor or virus according to any of the above aspects of the invention to a patient in need thereof.

SHORT DESCRIPTION OF THE FIGURES

DETAILED DESCRIPTION OF THE INVENTION

The invention reported herein provides evidence that miR-323-3p is involved in the pathogenesis of rheumatoid arthritis. The importance of miR-323-3p in the pathogenesis of rheumatoid arthritis was highlighted by the following aspects:

it was found that miR-323-3p is significantly increased in rheumatoid arthritis and thereby involved in the upregulation of proinflammatory cytokines and matrix metalloproteinases in synovial fibroblasts from patients with rheumatoid arthritis (RASF);

miR-323-3p also potentiates cell migration, proliferation and adhesion, other key processes in the pathogenesis of RA;

miR-323-3p directly targets and downregulates TIMP-3. TIMP-3 is a master regulator not only of MMP inhibition, but is also involved in the inhibition of IL-6 and TNFa activation via inhibition of the IL-6 sheddases and TNFa activator TACE.

In light of these data, the inhibition of MIR-323-3p combines the benefits of the best RA therapies currently available. The miR-323-3p modulator of the invention targets both the TNFa and IL-6 cytokine driven pathway and the cytokine-independent pathway of joint destruction mediated by synovial fibroblasts through the production of MMPs.

EXAMPLES

Figure 1:
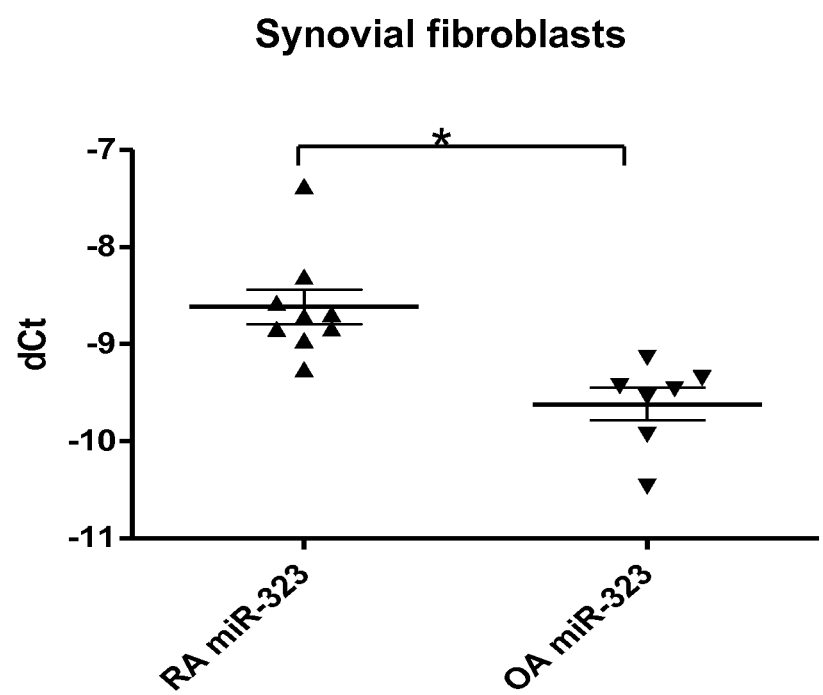
FIG. 1 shows the expression levels of miR-323-3p in RASF v. osteoarthritis synovial fibroblasts (OASF) as measured by real time PCR, normalised to let7A endogenous control.

Evaluation of expression of miR-323-3p in RASF vs. osteoarthritis (OA) synovial fibroblasts (OASF) shows (see FIG. 1) that levels of miR-323-3p as measured by Real time PCR and normalised to let7A endogenous control are significantly higher in synovial fibroblasts from rheumatoid arthritis patients (n=9) compared to osteoarthritis (n=7).

Figure 2:
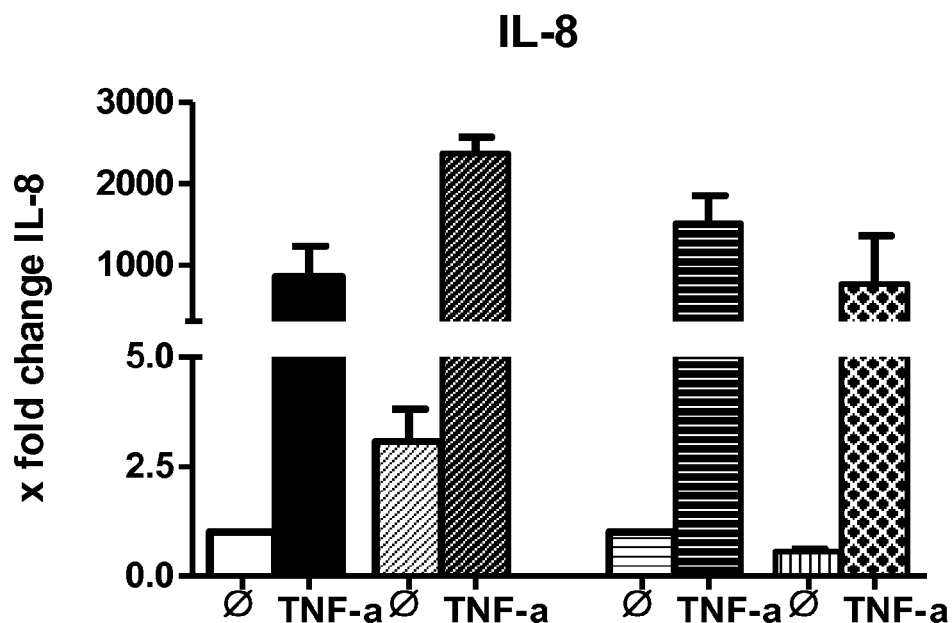
FIG. 2 shows cytokine mRNA expression by RASF in absence or presence of TNF alpha (each column pair: absence of TNF a: Ø (eft); presence of TNFa: (right)) for IL-8 (A) and IL-6 (B) in the presence of control (left column pair), miR-323-3p (second from left), an antagonist control (third) and an antagonist of miR-323-3p (right column pair). The x-axis shows n-fold increase of expression.
Figure 2:
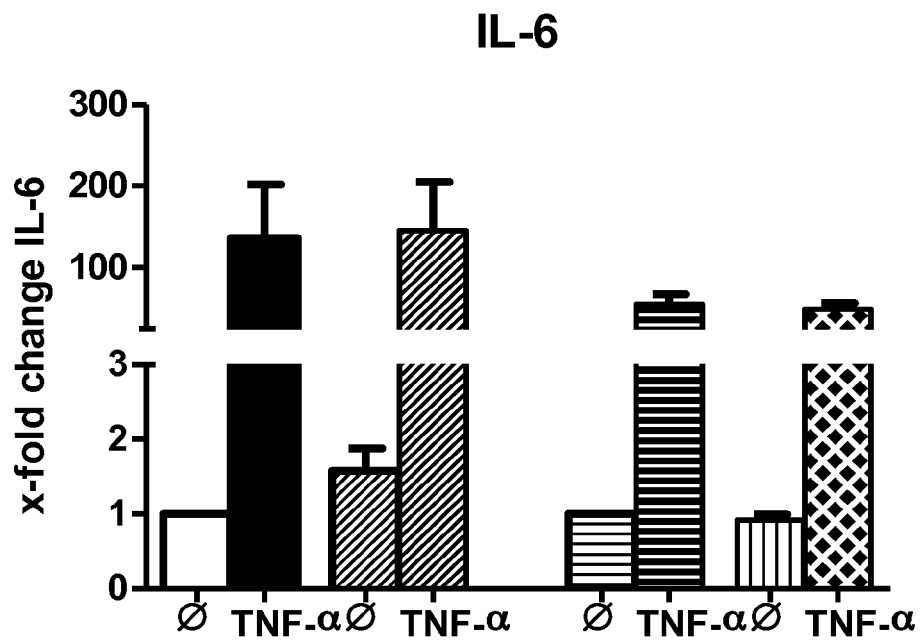
Figure 3:
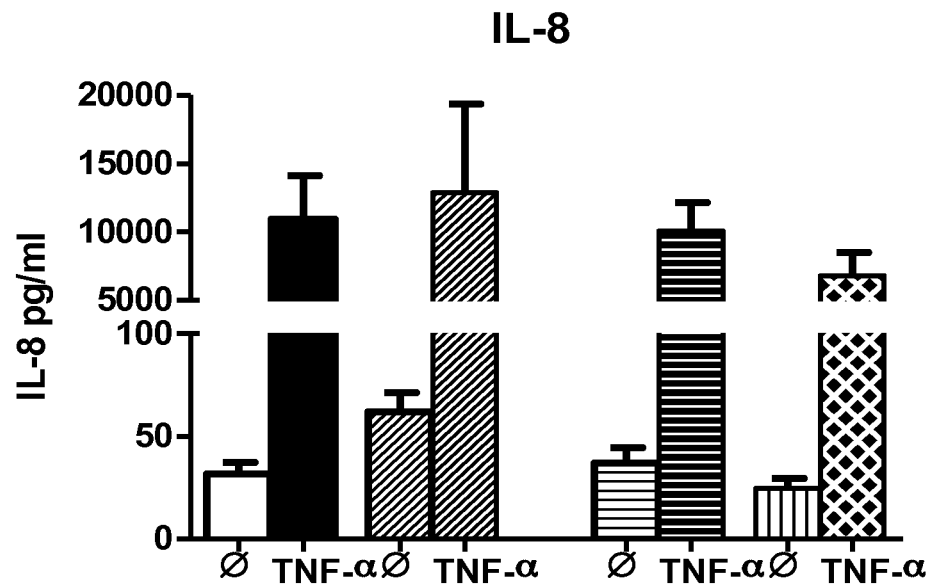
FIG. 3 shows cytokine protein expression by RASF in absence or presence of TNF alpha; same order of data as FIG. 2.
Figure 3:
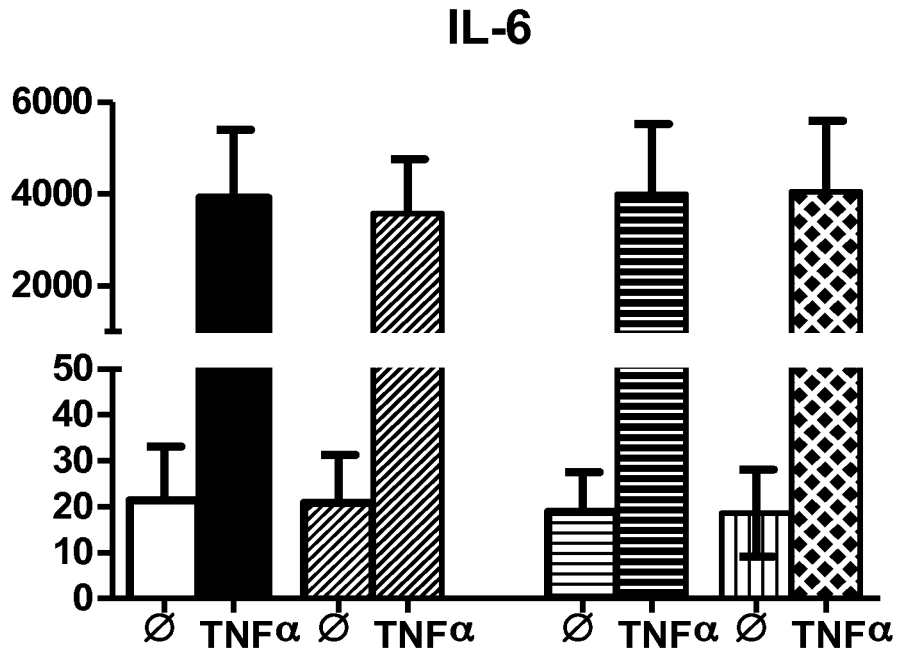

Modulation of cytokine mRNA (FIG. 2) and protein (FIG. 3) expression with miR-323-3p was analysed by quantitative RT-PCR and ELISA. Transfection of RASF with pre-miR-323 (100 nM) alone and in combination with TNFα (10 ng/ml) stimulation increases IL-8 mRNA (FIG. 2A) and protein (FIG. 3A) levels. Conversely, transfection of cells with anti-miR-323 (100 nM) decreased IL-8 transcript and protein expression. No effect was observed in IL-6 cytokine (FIG. 2B) or protein (FIG. 3B) levels following cell transfection of miR-323, either alone or in the presence of TNFα.

Figure 4:
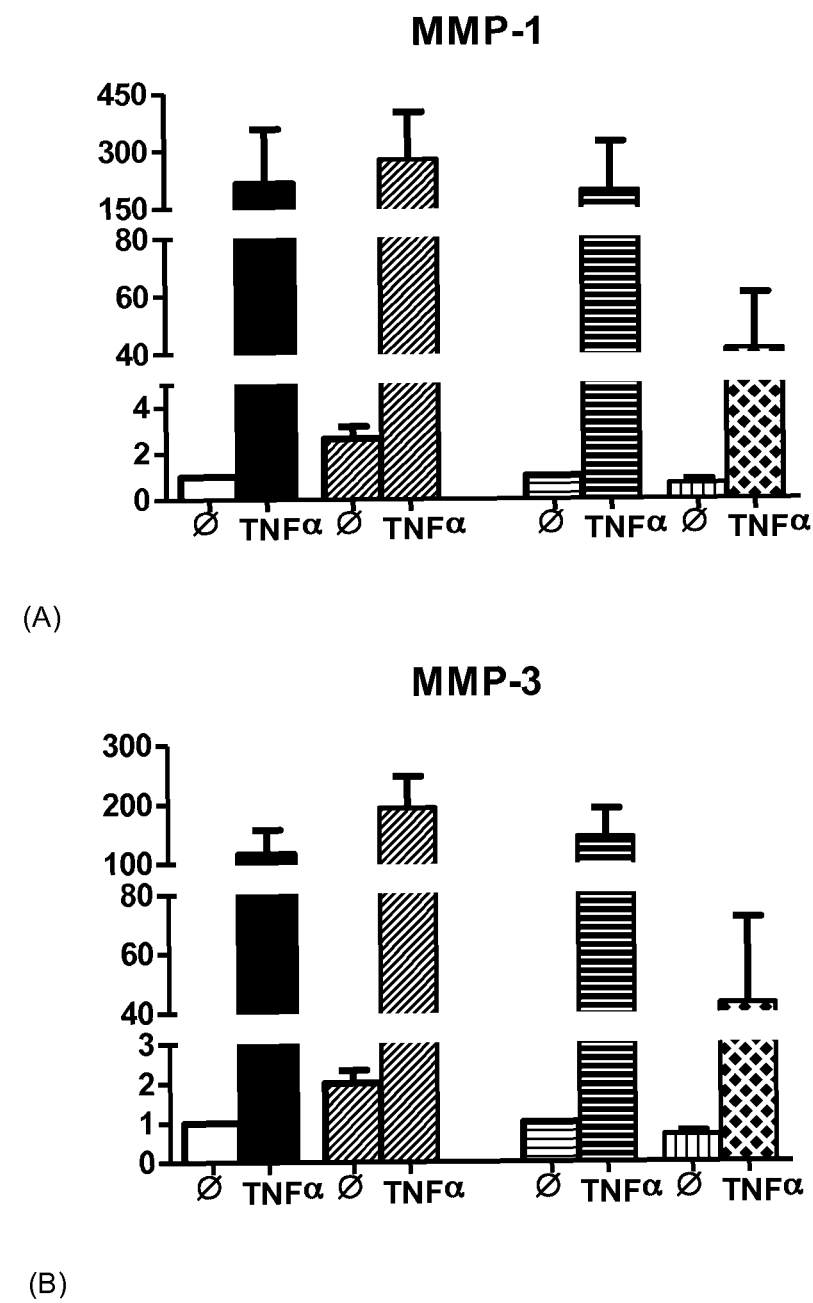
FIG. 4 shows matrix metalloproteinase RNA expression by RASF in absence or presence of TNF alpha; same order of data as FIG. 2.
Figure 5:
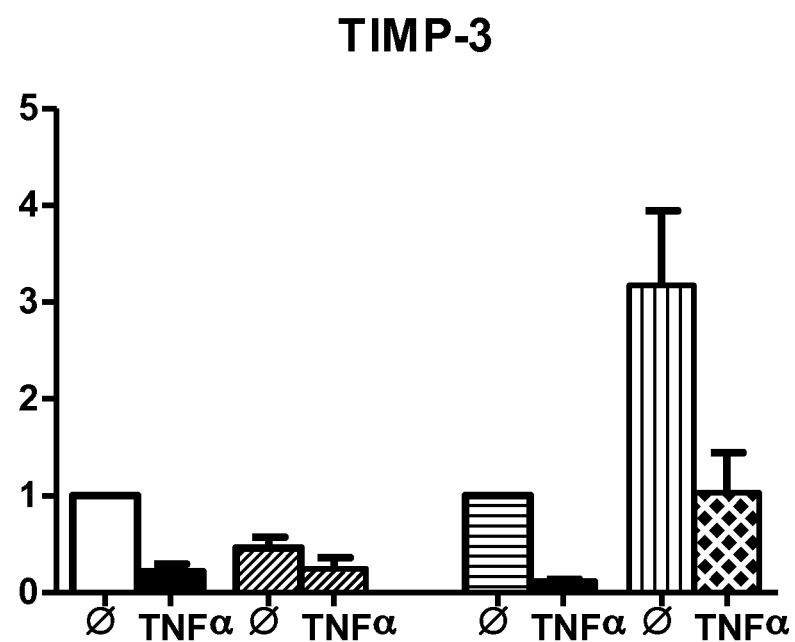
FIG. 5 shows tissue inhibitor of matrix metalloproteinase (TIMP) RNA expression by RASF in absence or presence of TNF alpha; same order of data as FIG. 2.
Figure 6:
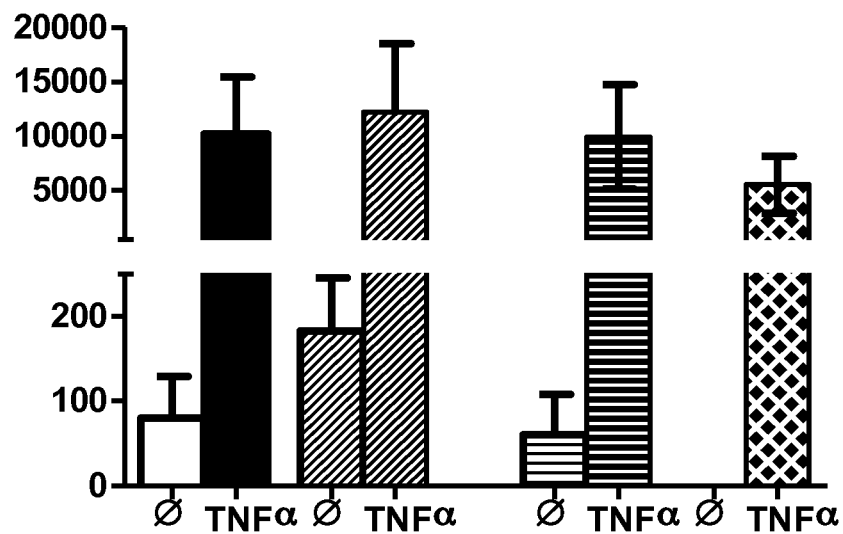
FIG. 6 shows matrix metalloproteinase protein expression by RASF in absence or presence of TNF alpha; same order of data as FIG. 2.
Figure 6:
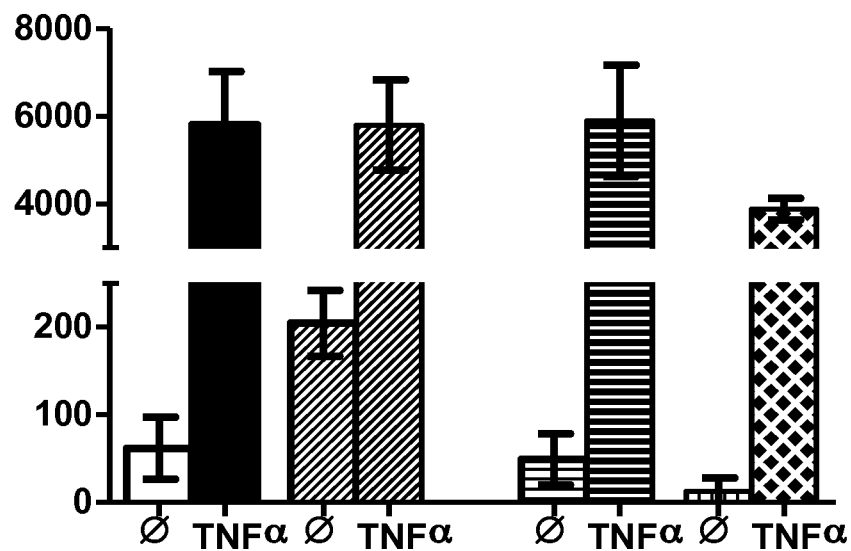

Modulation of MMP mRNA (FIG. 4) and protein (FIG. 6) expression with miR-323-3p was analysed by quantitative RT-PCR and ELISA. Transfection of RASF with pre-miR-323 (100 nM) alone and in combination with TNFa (10 ng/ml) stimulation increases MMP-1 (FIG. 4A) and MMP-3 (FIG. 4B) mRNA levels. Conversely, transfection of cells with anti-miR-323 (100 nM) decreased transcript levels of both MMPs. TIMP-3 mRNA is markedly upregulated upon inhibition of miR-323 (FIG. 5). Protein expression of MMP-1 (FIG. 6A) and MMP-3 (FIG. 6B) following transfection of RASF with pre and anti-miR-323, alone and in combination with TNFα stimulation shows a similar trend.

Figure 7:
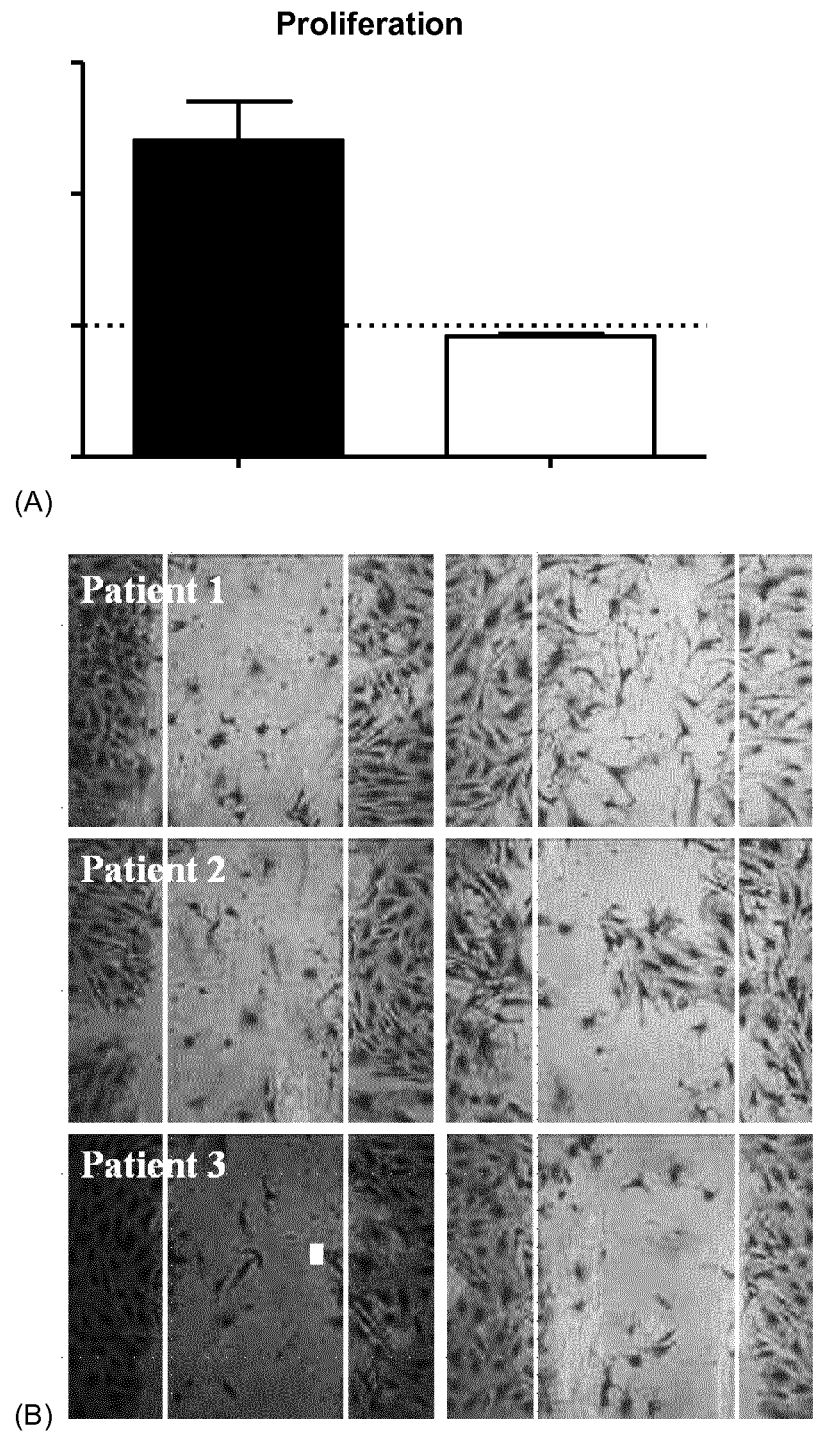
FIG. 7 shows (A) RASF cell proliferation in the presence of miR-323-3p (left bar) or its inhibitor (right bar) (Y-axis values represent n-fold increase; values are expressed as the mean.+-.SEM); (B) RASF cell migration induced by pre-miR-323.
Figure 8:
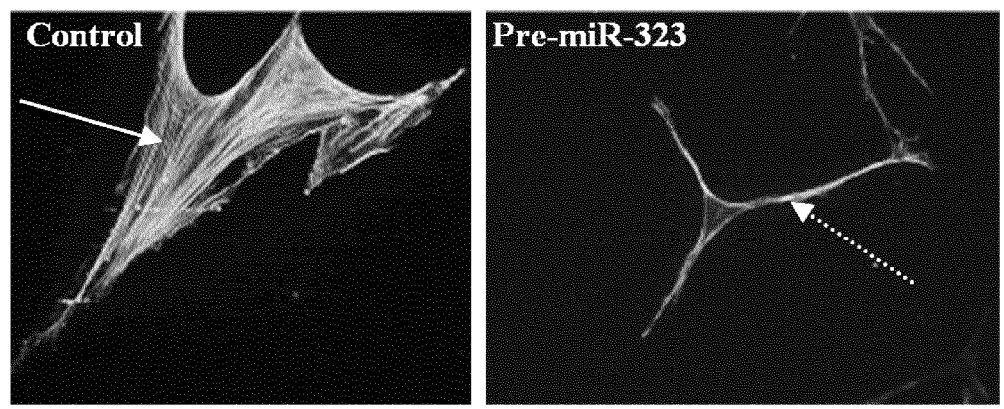
FIG. 8 shows the rearrangement of the actin cytoskeleton following overexpression of miR-323.

Pre-miR-323 increases cell proliferation (FIG. 7A) and migration (FIG. 7B) The induction by cytoskeletal rearrangement of the actin cytoskeleton following overexpression of miR-323 is evidenced by FIG. 8. White arrow (left) shows intact actin as observed in unstimulated control cells. Pre-miR-323 induces actin rearrangement and induces lamellopodia formation (broken arrow, right).

Figure 9:
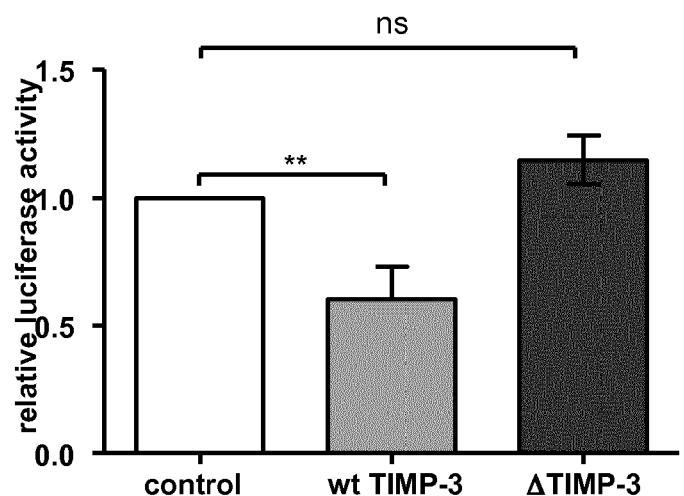
FIG. 9 shows luminescence readings of HEK293 cells after treatment with miR-323-3p. Values are expressed as the mean±SEM. **$p<0.01$

TIMP-3 is a direct target of miR-323-3p. HEK293 cells were transfected with a luciferase vector containing the wildtype 3' UTR of TIMP-3 or a 3' UTR with a mutation in the miR-323-3p seed sequence as negative control (ΔmiR-323). Transfection of the 3'UTR of TIMP-3 sense construct with pre-miR-323 (wt) resulted in lower relative luciferase activity as compared with mock transfected HEK cells (control) (FIG. 9). No effect of pre-miR-323 was seen in the mutated 3' UTR. Values are expressed as the mean±SEM. **$p<0.01$ Methods Synovial fibroblasts (SF) were isolated from RA and OA patients undergoing joint replacement surgery. Total RNA was isolated using the mirVana™ miRNA isolation kit. MiR-323-3p levels were analyzed by real-time PCR and data was calculated by the dCt method using miR-let-7a as an endogenous control. Over expression/silencing of miR was analysed using a synthetic precursor of Pre or a synthetic miR-323 inhibitor (Anti-miR™-323, Ambion respectively. Cytokine and MMP levels were measured by PCR and ELISA. Cell migration, adhesion and proliferation were examined using scratch, fibronectin-based adhesion or MTT assays. Cytoskeletal rearrangement was examined by immunofluorescent staining of filamentous actin (F-actin). The 3'UTR of TIMP-3 was cloned into a luciferase vector and reporter gene assays were carried out in pre-miR-323 transfected HEK293 cells.

The invention claimed is:

1. A method for treating rheumatoid arthritis in a patient in need thereof, comprising administering to the patient a miR-323-3p inhibitor comprising a hybridizing sequence of nucleotides at least 90% identical to reverse complementary sequence of SEQ ID 1 or SEQ ID 2; thereby treating the rheumatoid arthritis.

2. The method of claim 1, wherein the hybridizing sequence comprises deoxynucleotides.

3. The method of claim 1, wherein the hybridizing sequence comprises LNA and/or PNA nucleotides.

4. The method of claim 1, wherein the hybridizing sequence comprises phosphothioate and/or 2'-O-methyl-modified phosphothioate nucleotides.

5. The method of claim 1, wherein the hybridizing sequence is covalently attached to a cholesterol moiety or a peptide.

6. The method of claim 1, wherein the miR-323-3p inhibitor is a component of a pharmaceutical composition further comprising a pharmaceutically acceptable carrier and/or excipient.

7. A method for treating rheumatoid arthritis in a patient in need thereof, comprising administering to the patient a virus particle comprising:
   a nucleotide sequence capable of forming a hybrid to SEQ ID 1 or SEQ ID 2, wherein the nucleotide sequence is the reverse complement of a nucleotide sequence that is 90% identical to SEQ ID 1 or SEQ ID 2, and wherein the nucleotide sequence hybridizes to miR-323-3p or its precursor, thereby inhibiting expression of miR-323-3p, and thereby treating the rheumatoid arthritis.

8. The method of claim 7, wherein the virus is an adenovirus or adeno-associated virus.

9. The method of claim 7, wherein the virus is a component of a pharmaceutical composition further comprising a pharmaceutically acceptable carrier and/or excipient.

* * * * *

SEQUENCE LISTING

<160> NUMBER OF SEQ ID NOS: 2

<210> SEQ ID NO 1
<211> LENGTH: 21
<212> TYPE: RNA
<213> ORGANISM: Homo sapiens

<400> SEQUENCE: 1
cacauuacac ggucgaccuc u                                          21

```
<210> SEQ ID NO 2
<211> LENGTH: 86
<212> TYPE: RNA
<213> ORGANISM: homo sapiens

<400> SEQUENCE: 2
uugguacuug gagagaggug guccguggcg cguucgcuuu auuuauggcg cacauuacac    60
ggucgaccuc uuugcaguau cuaauc                                        86
```